United States Patent [19]

Raines

[11] Patent Number: 4,683,916
[45] Date of Patent: Aug. 4, 1987

[54] NORMALLY CLOSED AUTOMATIC REFLUX VALVE

[75] Inventor: Kenneth C. Raines, Bethlehem, Pa.

[73] Assignee: Burron Medical Inc., Bethlehem, Pa.

[21] Appl. No.: 911,419

[22] Filed: Sep. 25, 1986

[51] Int. Cl.⁴ .............................................. F16K 15/14
[52] U.S. Cl. ................................ 137/854; 251/149.1;
                                                         604/247
[58] Field of Search ........................ 137/843, 852, 854;
                                           251/149.1, 149.7; 604/247

[56] References Cited

U.S. PATENT DOCUMENTS

| | | | |
|---|---|---|---|
| 2,299,643 | 10/1942 | Moody | 251/149.1 |
| 4,143,853 | 3/1979 | Abramson | 251/149.1 |
| 4,387,879 | 6/1983 | Tauschinski | 251/149.1 |
| 4,535,820 | 8/1985 | Raines | 137/854 |

*Primary Examiner*—Robert G. Nilson
*Attorney, Agent, or Firm*—Shoemaker and Mattare, Ltd.

[57] ABSTRACT

A normally closed, one-way check valve having a body composed of two cylindrical containers which complement each other, each of said containers having a tubular projection with a liquid opening therethrough, one of said cylindrical chambers provided with a plurality of longitudinally extending ribs therealong for preventing sticking of a valve disc as contained within an assembled valve device, also further including a traverse bar for pressing against a valve disc. The other body component is provided with a pointed triangular support and also a plurality of radially extending ribs for preventing a valve disc from opening so far as to close off the egress port provided with said second element, together with a rubber resilient valve disc which is retained between the pointed triangular support and the traverse bar when the unit is assembled by sonic welding into a permanently assembled device. The assembled device further includes a circumferential ring having a pair of projecting legs, each leg having a rib on the free end thereof for reinforcement and direct engagement with the resilient valve disc for the purpose of opening same when the ring is moved under the force of the tip of a syringe.

17 Claims, 3 Drawing Figures

NORMALLY CLOSED AUTOMATIC REFLUX VALVE

BACKGROUND OF THE INVENTION

1. Field of the Invention

This invention relates generally to backflow check valves for use with liquid flow and administration apparatus for medical purposes.

2. Description of the Prior Art

A common problem of known devices of the conventional type is that upon reversal of liquid flow through tubing from a hypodermic syringe or the like, the known type check valves fail to respond as quickly as desired to the closed position. That is, there is always the risk of backflow from the output to the input, which in many instances is very undesirable, and in some cases, even deadly.

There have been devices made to be normally closed and under stress, whereby the valve in order to remain open must be subject to a high flow pressure, and thus when the flow pressure is decreased, the valve will quickly close. This is a great improvement over the afore-mentioned check valve; however, it still can be improved upon. The disadvantage of this type is that the valve disc itself may tend to move off center and thus have a tendency to bind an edge against one of the peripheries of the enclosing wall.

Other devices comprising one-way valves that are normally in the closed position fail to permit injection and aspiration when attached to a syringe.

Existing prior art patents which may be pertinent to the present invention are as follows:

| Raines | U. S. Pat. No. | 4,535,820 | 8/20/85 |
|---|---|---|---|
| Mackal, et al. | U. S. Pat. No. | 3,831,629 | 8/27/74 |
| Steer, et al. | U. S. Pat. No. | 3,570,484 | 3/16/71 |
| Harautuneian | U. S. Pat. No. | 3,385,301 | 5/28/68 |
| De See | U. S. Pat. No. | 3,192,949 | 7/6/65 |

U.S. Pat. No. 4,535,820 was invented by the same inventor as the present invention, and assigned to the same assignee as the present application. However, in this device the valve is normally closed and does not have structure therewith for permitting quick and easy injection and aspiration of fluids when the device is attached to a syringe. The purpose of the present invention is to overcome this.

The Mackal, et al. device (U.S. Pat. No. 3,831,629) is for a two-piece check valve having a reciprocable valve element. A liquid-injecting syringe can be used with this device.

U.S. Pat. No. 3,570,484 to Steer is a device for administering intravenous injections of liquids. A valve body has a non-return valve therein together with a plunger which when depressed will open the valve. However, the structure of this device is quite a bit different from that of the present invention.

U.S. Pat. Nos. 3,385,301 and 3,192,949 disclose valve elements which can be opened by insertion of a syringe 50 and 36 into the respective devices.

None of the known prior art devices offer the new and novel features of the present invention.

SUMMARY OF THE INVENTION

An object of the present invention is to provide a normally closed, high pressure check valve for use with administration of fluids and medicinal liquids in medical environments, together with structure for permitting injection and aspiration of fluids when the valve is attached to a syringe.

Another object of the present invention is to provide a one-way check valve structure including a flexible resilient disc which is maintained centered within the working body of the device, and prevented from movement off center of a central axis thereof, and/or frictional restraint or binding of a peripheral edge of the disc, together with a contiguous ring having depending legs for opening the valve disc when a syringe tip is inserted into the valve.

A further object of the present invention is to provide a high pressure check valve which is normally closed, which can be very quickly opened and just as quickly closed to prevent backflow of liquid being administered, and which has specific structure for opening the valve disc by inserting a tip of a syringe thereinto so that fluids can be injected and/or aspirated quickly and easily through the valve.

A still further object of the present invention is for a one-way check valve which is very quick acting, and structurally arranged so that no interference can occur through side movement of the valve disc within the valve body. Included with the valve is a ring and leg structure which, when engaged by the tip of a syringe, can be used to open the valve disc and permit fluid flow in either direction through the valve. Upon removal of the syringe tip, the valve disc snaps into the closed position.

The present invention provides a number of new and novel features over the check valves presently in use. A two-part body, each part having a cylindrical container portion therewith, when assembled restrains a flexible valve disc therewithin. A pointed triangle with one body element supports the central area of the disc, which in turn is under pressure from a traverse bar mounted in the other body element. The pressure between the triangle point and the bar generally is sufficient so the flexible disc will be restrained against sideways movement.

To further assure that no peripheral edge binding of the flexible disc can occur, longitudinally extending ribs are preferably provided within the inner wall of the body element most closely surrounding the valve disc. Such ribs, being spaced quite far apart and relatively small in width, permit almost as much fluid flow as a valve without such ribs, but greatly increase the assurance of free flexible movement of the valve disc periphery without binding.

Further included in the check valve of the present invention is a small plastic plunger comprising a circular contiguous ring slidably mounted in the other body element and having a pair of depending legs which are adapted to rest adjacent the upper surface of the valve disc. Upon engagement of the ring portion of the structure by the tip of a syringe, or other injection device, this structure can be moved slidably relative to the body elements and into engagement of the legs with the valve disc, which in turn will open the disc and permit fluid flow through the valve. Thus, the addition of this structure to the original device of applicant greatly improves operation of same.

These together with other objects and advantages which will become subsequently apparent reside in the details of construction and operation as more fully hereinafter described and claimed, reference being had to the accompanying drawing forming a part hereof, wherein like numerals refer to like parts throughout.

DETAILED DESCRIPTION OF THE PREFERRED EMBODIMENTS

Figure 1:
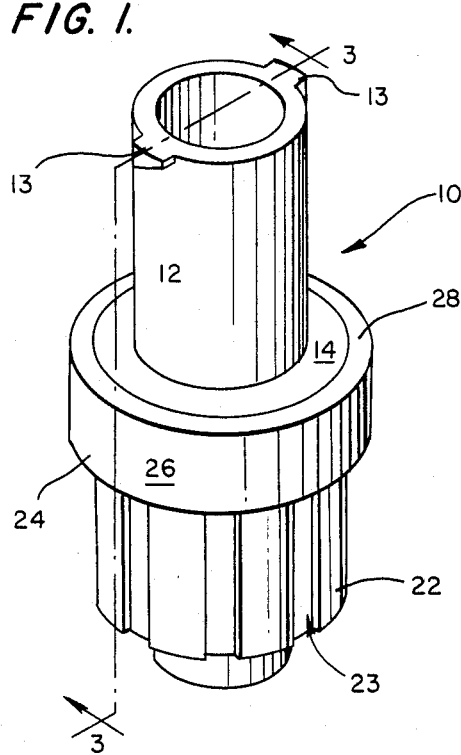
FIG. 1 is a perspective view of the assembled device of the present invention.

Referring to FIG. 1 of the drawing, reference numeral 10 indicates in general the present invention. The one-way, normally closed check valve of the present invention includes a valve body made of two component body elements. One element 11 has a tubular portion 12 terminating in an enlarged container 16. Locking ears 13 are provided at one end of tubular portion 12, while the container portion 16 at the other end has an upper surface or shoulder 14 and an outer or lower surface 18. A traverse cross bar 15 is formed within this element, with the axis thereof being in line with the surface 14. A longitudinal inlet opening 17, preferably having a female taper 117, extends through tubing 12 into the interior of container 16. The inner circumferential wall of the container 16 is provided with a plurality of longitudinally extending ribs 19. These ribs are for the specific purpose of preventing binding of the peripheral edge of the flexible valve disc as contained within this body portion of the valve after assembly with the other body element 25.

Figure 3:
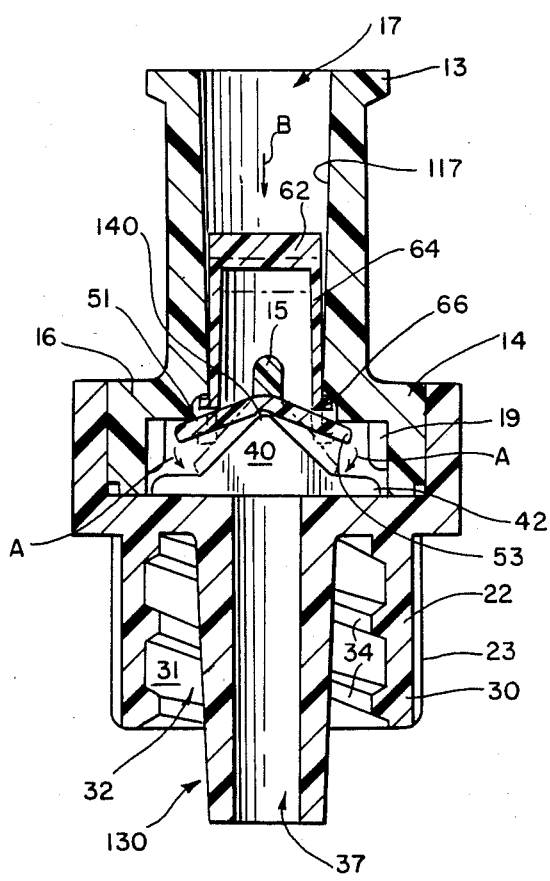
FIG. 3 is a cross-sectional view taken generally along line 3—3 of FIG. 1.

The other body element 25 for the valve comprises a can 26 having an upper surface 28 and a lower shoulder 24, integral with a double tubular extension 22 and 30, best seen in the cross-sectional view of FIG. 3. Within the outer tubular portion 22 is an inner wall 31 provided with threads 34 for attachment to appropriate flow structure. The central tubular portion 30 is provided with an inner outlet opening 37 therethrough and an outer male luer taper 130. Recesses 23 also are provided in the outer circumference of outer tubular portion 22.

The valve disc per se is a circular disc 50 provided with opposite surfaces 51 and 53, both of which are substantially flat. The disc 50 preferably is made of flexible yet resilient rubber or rubber-like material.

A triangular pointed member 40 having extending ribs 42 therewith is molded or integrally affixed to the lower body element 26. Additional radial supporting ribs 142 are preferably also integrally formed with this body element. The purpose of ribs 42, 142 is to assure that when the flexible disc is completely open, as indicated by the dotted lines, an adequate space will always remain for liquid flow (see arrows A) about the peripheral edge of the disc and above the surface 126 of the larger body element.

An additional member 60 is included with the foregoing elements for the purpose of permitting opening of the valve disc 50 by the tip of a syringe. This member comprises a circumferential ring 62 having integrally formed legs 64 extending therefrom. The tip edges of these legs are provided with enlarged ribs 66 at the free ends thereof. As best seen in FIG. 3, a circumferential recess 166 is provided within the enlarged container 16 of the one element 11. Recess 166 receives ribs 66 and retains member 60 with element 11. In the normal position the valve disc 50 will be closed as shown in FIG. 3; however, upon engagement of the ring 62 by the tip end of a syringe, a user of the device can push the member 60 in the direction of arrow B to open the valve disc 50. The dotted lines in FIG. 3 show this valve disc as opened by the ends of legs 64 and ribs 66.

Figure 2:
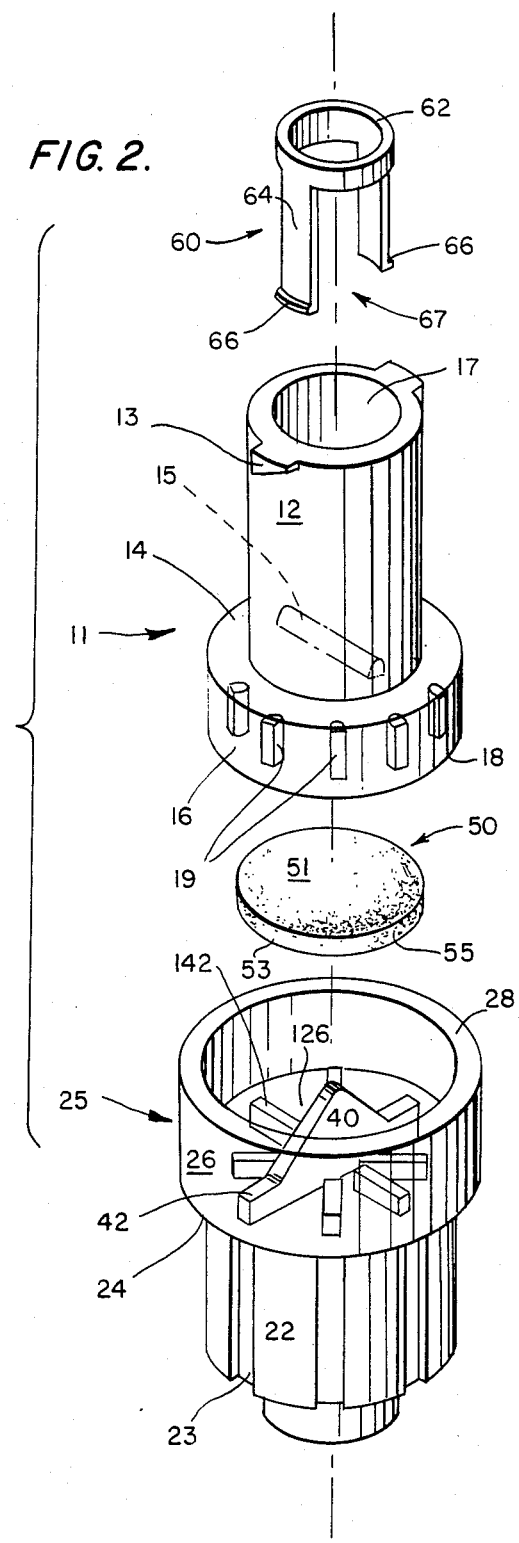
FIG. 2 is an exploded perspective view of the component elements of the present invention as disassembled.

After the component elements of FIG. 2 are assembled into position as shown in FIG. 3, sonic welding SW is preferably used to securely fasten the two body components into a single integral unit. Once assembled, the device cannot be again disassembled without complete destruction of the device.

Upon assembly, the lower surface of the traverse bar 15 of the upper (as shown) first body element firmly presses against the mid-portion of the flexible disc and presses same against the upper tip of triangular point 40. Preferably, the pressure is such that the triangular tip will form a small indentation 140 (FIG. 3) within the disc. This indentation 140 then will positively restrain the disc from sideways movement. However, if any sideways movement should occur, or if during assembly the disc happens to move slightly off center so that one peripheral edge tends to engage against the inner circumferential wall of container 16, the longitudinal ribs 19 within container 16 will assure that no frictional binding will take place.

The present invention offers a number of important advantages over the known prior art. By positively assuring that the flexible disc is always centered, and cannot move sideways of the body container, positive and efficient one-way check action of the valve device is assured. In addition, providing the ring with depending legs for the purpose of permitting a user to insert a syringe into the valve device and thereby open the valve disc to permit fluid passage through the valve is very advantageous in actual use. While the structural differences over known prior art may seem small, the difference is quite significant in actual practice.

The foregoing is considered as illustrative only of the principles of the invention. Further, since numerous modifications and changes will occur to those skilled in the art, it is not desired to limit the invention to the exact construction and operation shown and described, and accordingly, all suitable modifications and equivalents may be resorted to falling within the scope of the invention.

I claim:

1. A valve device comprising:
    a first body element having an input opening therethrough;
    a second body element which complements said first body element and having an outlet opening therefrom;
    a resilient valve disc mountable between said first and second body elements;
    first means with one body element for supporting the disc at the center thereof;
    means with the other body element for holding said disc firmly against said first means in such a manner that said disc is restrained from sideways movement; and
    means adjacent said valve disc for engagement by a syringe to open said normally closed disc to permit injection and aspiration of fluids through the device.

2. The valve of claim 1, wherein said means for opening said normally closed disc includes a circumferential ring having a pair of legs projecting therefrom for contact with said valve disc when the ring is depressed by the tip of a syringe inserted thereinto.

3. The valve of claim 2, wherein said projecting legs are provided with enlarged ribs at the free end thereof.

4. The valve of claim 3, together with further means for preventing the disc from blocking the path of fluid flow in the open direction thereof.

5. The valve of claim 4, together with additional means for preventing the circumferential edge of the disc from binding or sticking against the sides of the body element it is most closely adjacent to.

6. The valve of claim 5, wherein said means for preventing the disc edge from binding against the sides of the body element comprise ribs which extend lengthwise of the inner circumferential wall of said body element.

7. The valve of claim 2, wherein said further means for preventing the disc from blocking the path of fluid flow include a plurality of radially extending ribs along the floor of the other body element having the outlet opening therethrough.

8. The valve of claim 1, wherein said means with one body element for supporting the disc at the center thereof comprises a pointed triangular member which makes a depression directly in the smooth surface of the flexible rubber valve disc.

9. The valve of claim 8, wherein said valve disc is normally flat on both surfaces and is only deformed at the center thereof under pressure between said first and second means.

10. A normally closed one-way check valve comprising: a first cylindrical chamber having an opening centrally thereof; a second cylindrical chamber having an opening centrally thereof, said first cylindrical chamber having a slightly smaller external diameter than the internal diameter of said second cylindrical chamber so that it complements and fits inside thereof for forming an overall closed chamber body element; one of said cylindrical chambers provided with a traverse bar thereacross; the other cylindrical chamber provided with a pointed support member; a resilient disc mounted in compression between said pointed support member and said traverse bar in such a manner that a depression is made in the central area of said disc so that said disc is restrained from sideways movement within the valve body element chamber; and means provided within said first cylindrical chamber for opening the normally closed resilient disc.

11. The normally closed one-way check valve of claim 10, wherein said disc is normally flat on both sides except for the central area which is slightly deformed during assembly of the component elements of the valve device.

12. The normally closed one-way check valve of claim 10, wherein said means for opening said resilient disc includes a body structure having projections extending therefrom for direct engagement with said resilient disc when it is depressed by external force being applied thereto.

13. The normally closed one-way check valve of claim 10, wherein said means includes a circular ring having a pair of projecting legs extending therefrom for engagement with said resilient disc when said ring is moved by pressure from external means applied thereto.

14. The normally closed one-way check valve of claim 10, wherein said opening in said first cylindrical chamber comprises a tubular projection having a female luer input taper thereto and retainer projections externally thereof.

15. The normally closed one-way check valve of claim 14, wherein said second cylindrical chamber is provided with dual integral tubular projections, one of said integral tubular projections including the central opening therethrough, and the other integral tubular projection being internally threaded for receiving liquid flow structure connected thereto.

16. The normally closed one-way check valve of claim 10, wherein said body component elements are sonically welded together to provide a non-disassembleable valve device.

17. The normally closed one-way check valve of claim 16, wherein said resilient valve disc is made of rubber material.

* * * * *